United States Patent [19]

Dautzenberg et al.

[11] 4,247,718

[45] Jan. 27, 1981

[54] PROCESS FOR THE PREPARATION OF α-β UNSATURATED ALCOHOLS

[75] Inventors: Jozef M. A. Dautzenberg; Joannes M. C. A. Mulders; Petrus A. M. J. Stijfs, all of Geleen, Netherlands

[73] Assignee: Stamicarbon, B.V., Geleen, Netherlands

[21] Appl. No.: 20,044

[22] Filed: Mar. 13, 1979

[30] Foreign Application Priority Data

Mar. 13, 1978 [NL] Netherlands .................. 7802694

[51] Int. Cl.³ .............................................. C07C 29/14
[52] U.S. Cl. ..................................... 568/654; 568/813
[58] Field of Search ..................... 568/814, 654, 813

[56] References Cited

U.S. PATENT DOCUMENTS

| 3,280,192 | 10/1966 | Levy et al. | 568/814 X |
| 4,073,813 | 2/1978 | Cordier | 568/814 |

Primary Examiner—Bernard Helfin
Attorney, Agent, or Firm—Cushman, Darby & Cushman

[57] ABSTRACT

An improved process for the preparation of α-β unsaturated alcohols by the liquid phase catalytic hydrogenation of the corresponding aldehyde. An aldehyde is selected having the general formula

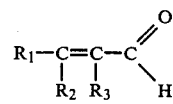

wherein at least one of $R_1$, $R_2$ and $R_3$ is an unsubstituted phenyl group or a phenyl group substituted with alkyl and/or alkoxy groups wherein the carbon atoms of the substituents on any phenyl group total no more than five, and the remainder of said $R_1$, $R_2$ and $R_3$ independently represents hydrogen or an alkyl group having from 1 to 10 carbon atoms. The selected aldehyde is hydrogenated in the presence of a platinum catalyst in a liquid reaction medium of water and a water-immiscible organic solvent, wherein an alkali metal hydroxide and/or an alkali metal alkoxide promoter is dissolved in the water.

9 Claims, No Drawings

PROCESS FOR THE PREPARATION OF α-β UNSATURATED ALCOHOLS

BACKGROUND OF THE INVENTION

The invention relates to an improved process for preparing α-β unsaturated alcohols by the liquid phase catalytic hydrogenation of the aldehyde corresponding to the desired alcohol. Alcohols of this type are of commercial importance as starting materials in the flavor and fragrance industry.

When an α-β unsaturated aldehyde is hydrogenated to prepare the corresponding alcohol, the hydrogenation must be effected preferentially so that little or no hydrogenation of the double bond in question occurs. To achieve this, various catalysts have been proposed for this hydrogenation. The catalyst recommended in U.S. Pat. No. 3,284,517 is platinum on carbon with divalent iron and silver as promoters. According to British Pat. No. 1,123,837 platinum with an alkali hydroxide or alkali metal alkoxide as a promoter is very suitable as a catalyst. However, U.S. Pat. No. 3,655,777 states that platinum is unsuitable as a catalyst, but that very good results can be obtained with osmium. British Pat. No. 1,439,711 describes the successful use of a platinum-cobalt catalyst.

When these known catalyst are used in conventional process for the preferential hydrogenation of α-β unsaturated aldehydes, the amount of catalyst required is relatively large and the conversion of the aldehyde is often incomplete. These known methods are therefore not very attractive economically.

DESCRIPTION OF THE INVENTION

It is an object of the present invention to provide an improved process for the hydrogenation of α-β unsaturated aldehydes to the corresponding alcohols wherein the conversion is complete or virtually complete, and the catalyst consumption is considerably lower than in known processes. This is accomplished according to the process of the invention by hydrogenating a selected aldehyde having the general formula

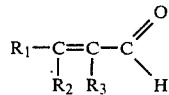

in which at least one of $R_1$, $R_2$ and $R_3$ represents an unsubstituted phenyl group or a phenyl group substituted with one or more alkyl and/or alkoxy groups wherein the carbon atoms of the substituents on any phenyl group total no more than five. The remainder of $R_1$, $R_2$ and $R_3$ independently represents either hydrogen or an alkyl group having from 1 to 10 carbon atoms. The hydrogenation is carried out in a reaction medium of water and a water-immiscible organic solvent and an alkali metal hydroxide and/or alkali metal alkoxide promoter is dissolved in the water phase.

Examples of aldehydes coming within the scope of the invention, which are very suitable for use in this process, include 3-phenyl-2-propenal (cinnamic aldehyde), 2-n-pentyl-3-phenyl-2-propenal, 2-n-hexyl-3-phenyl-2-propenal, 2-methyl-3-phenyl-2-propenal, 2-phenyl-2-pentenal, 2-phenyl-2-propenal, and 3-p-methoxyphenyl-2-propenal.

Various water-immiscible organic solvents may be used in the process of the invention, including benzene, xylenes, cyclopentane, cyclohexane, n-pentane and n-hexane. The preferred water-immiscible organic solvent is toluene. The ratio between the water and organic solvent may be carried over a wide range, such as between 0.05 and 3 grams of water per gram of organic solvent. However an amount of 0.2 to 1 gram of water per gram of organic solvent is particularly suitable.

The amount of organic solvent present per gram of aldehyde to be converted may also be chosen within relatively wide limits, such as between 0.25 and 20 grams of organic solvent per gram of aldehyde to be converted. However preferably the amount of organic solvent will be between 0.5 and 5 grams per gram of aldehyde to be converted.

The catalyst may be any of the various platinum catalysts that are well known in hydrogenation. Preferably the platinum will be present in an amount corresponding to about 0.03 to 5 milligrams per gram of aldehyde to be converted, and most preferably about 0.05 to 2.5 milligrams of platinum per gram of aldehyde to be converted.

The amount of alkali metal hydroxide and/or alkali metal alkoxide dissolved in the water in the present process should be between about 0.1 and 0.7 mole, and most preferably between about 0.2 and 0.5 mole per 100 grams of water.

When carrying out the hydrogenation, the temperature should not be too high. Most suitable temperatures are below 60° C., and preferably between about −5 and 45° C. However the temperature should not be lower than the temperature at which solids start crystalizing from the liquid phase.

The hydrogen pressure during the hydrogenation is not critical. Good results are usually obtained using a partial hydrogen pressure of between about 500 and 30,000 kPa.

Upon completion of the hydrogenation, the liquid reaction medium may be separated into an organic layer containing the desired reaction product, and an aqueous layer containing the catalyst and the promoter used. This aqueous layer can be reused in the hydrogenation of further amounts of aldehyde, thereby permitting a substantial savings in catalyst consumed or otherwise lost in the process. The unsaturated alcohol may be recovered from the organic layer for instance by distillation and the organic solvent may be reused.

The process of the invention will be further illustrated by the following examples.

EXAMPLES I-XV

An amount of water in which alkali metal hydroxide or alkali metal alkoxide has been dissolved as a promoter is put into a 0.5-liter autoclave provided with a stirrer. An amount of commercially available platinum catalyst and a solution of the aldehyde to be hydrogenated in the organic solvent are then added to this alkaline solution. The autoclave is then closed, and the hydrogenation is carried out and the reaction conditions maintained until no more hydrogen is absorbed.

The organic phase containing the reaction product is then separated from the aqueous phase containing the catalyst. After neutralization of the organic phase with a small amount of acid, the organic solvent is evaporated. The residue is a crude reaction product from which the desired alcohol of olfactory grade can be obtained by distillation.

The starting material in Examples I–XIV is 60 grams of aldehyde. In Example XV the starting amount of aldehyde is 40 grams. Except in Example V, the organic solvent used is 100 grams of toluence. In Example V use is made of 100 grams cyclohexane. In all examples except Example VII, the catalyst used is platinum on carbon having 5% by weight of platinum. In Example VII a platinum-on-carbon catalyst is used having 10% by weight of platinum. The other reaction conditions and the results are shown in the table below. These results are based on gaschromatographic analyses.

EXAMPLE XVI

To the remaining aqueous phase containing catalyst resulting from Example I, an additional 0.06 gram of the same catalyst is added, and the amounts of promoter and water are made up to the original amounts of Example I. Example I is repeated using this aqueous phase. The results obtained are virtually the same to those of the original Example I.

In this way the residual aqueous solution in question can be reused many times, for example 20 times. It is found that when the hydrogenation is carried out in accordance with the process of this invention and the catalyst containing aqueous phase reused, on the average only about 0.05 milligram of platinum metal must be replenished per gram of 3-phenyl-2-propenal utilized.

selecting an aldehyde having the general formula

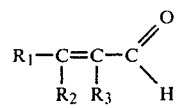

wherein at least one of $R_1$, $R_2$ and $R_3$ represents a member of the class consisting of an unsubstituted phenyl group and a phenyl group substituted with at least one substituent selected from the group consisting of alkyl and alkoxy groups wherein the carbon atoms of the substituents on any said phenyl group total no more than five, and the remainder of said $R_1$, $R_2$ and $R_3$ independently represents a member of the group consisting of hydrogen or an alkyl group having from 1 to 10 carbon atoms; and hydrogenating said selected aldehyde in a liquid reaction medium consisting essentially of water and a water-immiscible organic solvent, wherein a promoter selected from the group consisting of an alkali metal hydroxide, and alkali metal alkoxide and combinations thereof is dissolved in said water, resulting in the formation of an organic phase containing hydrogenated reaction product and an aqueous phase containing said catalyst and promoter;

Table

| example no. | aldehyde | temp. °C. | hydrogen pressure kPa | catalyst g | promoter |
|---|---|---|---|---|---|
| I | 3-phenyl-2-propenal | 20 | 12000 | 0.18 | 10.2 g KOH |
| II | 2-methyl-3-phenyl-2-propenal | 20 | 12000 | 0.18 | 10.2 g KOH |
| III | 2-hexyl-3-phenyl-2-propenal | 20 | 12000 | 0.18 | 10.2 g KOH |
| IV | 2-amyl-3-phenyl-2-propenal | 20 | 12000 | 0.18 | 10.2 g KOH |
| V | 3-phenyl-2-propenal | 20 | 12000 | 0.18 | 10.2 g KOH |
| VI | 3-phenyl-2-propenal | 20 | 12000 | 0.18 | 10 g $CH_3ONa$ |
| VII | 3-phenyl-2-propenal | 20 | 12000 | 0.09 | 10.2 g KOH |
| VIII | 3-phenyl-2-propenal | 40 | 12000 | 0.18 | 10.2 g KOH |
| IX | 3-phenyl-2-propenal | 20 | 12000 | 0.25 | 10.2 g KOH |
| X | 3-phenyl-2-propenal | 4 | 12000 | 0.50 | 10.2 g KOH |
| XI | 3-phenyl-2-propenal | 20 | 26000 | 0.18 | 10.2 g KOH |
| XII | 3-phenyl-2-propenal | 0 | 2000 | 3 | 6 g KOH |
| XIII | 3-phenyl-2-propenal | 37 | 2000 | 1 | 5.1 g KOH |
| XIV | 2-methyl-3-phenyl-2-propenal | 0 | 2000 | 3 | 6 g KOH |
| XV | 3-phenyl-2-propenal | 0 | 2000 | 2 | 5.1 g KOH |

| example no. | water g | reaction time h | conversion aldehyde % | yields in % α-β unsaturated alcohol | saturated alcohol | saturated aldehyde |
|---|---|---|---|---|---|---|
| I | 60 | 6 | 99.4 | 92.4 | 5.2 | 0.8 |
| II | 60 | 6 | 99.7 | 93.6 | 4.3 | 0.3 |
| III | 60 | 7 | 99.2 | 94.1 | 4.6 | 0.5 |
| IV | 60 | 7 | 99.6 | 93.2 | 4.8 | 0.6 |
| V | 60 | 6 | 99.1 | 91.6 | 5.8 | 1.0 |
| VI | 60 | 6 | 99.2 | 92.0 | 5.3 | 0.9 |
| VII | 60 | 7 | 98.7 | 91.1 | 5.8 | 1.2 |
| VIII | 60 | 4 | 98.9 | 83.1 | 8.3 | 1.4 |
| IX | 60 | 3 | 98.3 | 91.6 | 5.1 | 1.8 |
| X | 60 | 4 | 98.7 | 93.3 | 3.7 | 0.4 |
| XI | 60 | 3.5 | 97.1 | 94.1 | 3.6 | 2.0 |
| XII | 40 | 4 | 97.8 | 93.4 | 5.2 | 0.4 |
| XIII | 30 | 2.5 | 99.6 | 86.0 | 10.2 | 0.7 |
| XIV | 40 | 4 | 98.7 | 94.1 | 4.8 | 0.2 |
| XV | 40 | 4 | 99.5 | 89.2 | 6.5 | 0.2 |

What is claimed is:

1. An improved process for the preparation of α-β unsaturated alcohols by the liquid phase hydrogenation, in the presence of a platinum metal containing catalyst, of the aldehyde corresponding to the desired alcohol, said improvement essentially comprising:

separating said aqueous phase containing catalyst and promoter from said organic phase; and utilizing said separated aqueous phase for the hydrogenation of a further amount of said aldehyde.

2. The process of claim 1 wherein said water-immiscible organic solvent is toluene.

3. The process of claim 1 wherein 0.2 to 1 gram of water is used per gram of organic solvent.

4. The process of claim 1 wherein 0.5 to 5 grams of organic solvent are used per gram of aldehyde to be converted.

5. The process of claim 1 wherein said hydrogenation is carried out in the presence of a catalyst containing platinum in an amount of 0.05 to 2.5 milligrams of platinum per gram of aldehyde to be hydrogenated.

6. The process of claim 1 wherein said dissolved promoter is present in an amount of 0.2 to 0.5 mole per 100 grams of water.

7. The process of claim 1 wherein said hydrogenation is carried out at a temperature of between $-5°$ and $45°$ C.

8. The process of claim 1 wherein said hydrogenation is carried out at a partial hydrogen pressure of between 500 and 30,000 kPa.

9. The process of claim 1 wherein said aldehyde is selected from the group consisting of 3-phenyl-2-propenal, 2-n-pentyl-3-phenyl-2-propenal, 2-n-hexyl-3-phenyl-2-propenal, 2-methyl-3-phenyl-2-propenal, 2-phenyl-2-pentenal, 2-phenyl-2-propenal or 3-p-methoxyphenyl-2-propenal.

* * * * *